United States Patent [19]

Ishihara et al.

[11] Patent Number: 4,484,135
[45] Date of Patent: Nov. 20, 1984

[54] HEMATOCRIT MEASURING INSTRUMENT

[75] Inventors: Toshikazu Ishihara; Hazime Inagaki, both of Aichi, Japan

[73] Assignee: Kabushiki Kaisha Toyota Chuo Kenkyusho, Aichi, Japan

[21] Appl. No.: 406,878

[22] Filed: Aug. 10, 1982

[30] Foreign Application Priority Data

Aug. 18, 1981 [JP] Japan ................................ 56-129197

[51] Int. Cl.$^3$ ........................................... G01H 27/00
[52] U.S. Cl. .................................. 324/71.1; 128/632; 324/71.4; 324/439; 324/441; 604/66
[58] Field of Search ....................... 324/71.4, 62, 65 R, 324/425, 439, 444, 71.1; 128/632, 637, 670, 441, 635, 734; 436/70, 150; 356/39, 40, 41, 42; 604/66

[56] References Cited

U.S. PATENT DOCUMENTS

| | | | |
|---|---|---|---|
| 2,656,508 | 10/1953 | Coulter | 324/439 |
| 3,259,842 | 7/1966 | Coulter et al. | 324/439 |
| 3,831,083 | 8/1974 | Teass, Jr. et al. | 324/444 |
| 3,896,373 | 7/1975 | Zelby | 324/439 |
| 3,979,665 | 9/1976 | Ebling et al. | 324/449 |
| 4,300,551 | 11/1981 | Kinney | 128/637 |
| 4,374,644 | 2/1983 | Armstrong | 324/71.4 |
| 4,408,157 | 10/1983 | Beaubien | 324/62 |

Primary Examiner—Stewart J. Levy
Attorney, Agent, or Firm—Koda and Androlia

[57] ABSTRACT

A hematocrit measuring instrument of the type which determines hematocrit of blood from the electrical resistivity of the blood is provided with a blood resistivity measurement device, an ultrafilter for filtering a part of the plasma from the blood, a filtrate resistivity measurement device for measuring the resistivity of the filtrate from the ultrafilter and an arithmetic circuit for calculating the hematocrit of the blood from the resistivities of the blood and the filtrate. The hematocrit measuring instrument is connected into a circulatory path for the blood outside of the patient's body and continuously measures the hematocrit of the blood from the resistivity of the blood and the resistivity of the filtrate from the ultrafilter.

4 Claims, 5 Drawing Figures

HEMATOCRIT MEASURING INSTRUMENT

BACKGROUND OF THE INVENTION

1. Field of the Invention

This invention relates to a hematocrit measuring instrument, more particularly to an improved hematocrit measuring instrument capable of continuous measurement and capable of highly accurate measurement even in the case where there are variations in the concentration of the plasma electrolyte.

2. Description of the Prior Art

Measurement of the hematocrit of blood (the ratio of the volume of blood cells to the volume of the whole blood) is carried out as an effective technique in the diagnosis of diseases, medical treatment and health care. In view of the usefulness of this measurement there has been desired a better instrument for carrying it out.

Various instruments have been known for hematocrit measurement including those employing centrifugation, those which make the measurement from the blood cell count of a given volume (unit volume) of blood and the mean blood cell volume and those which make the measurement from the electrical resistance of the blood.

Among the hematocrit measuring instruments employing centrifugation, the type employing Wintrobe's method is generally considered to be standard. However, as this instrument performs the measurement using extracted blood specimens, it is not suitable for a system for carrying out measurements continuously.

The hematocrit measuring instruments which derive the hematocrit from the blood cell count and the mean blood cell volume are also unsuitable for carrying out measure continuously. More specifically, as they perform the measurement using diluted blood, if the concentration of the electrolyte and the protein in the diluted blood should differ from that in the blood plasma, the cell volume of the diluted blood will differ from the cell volume of the blood in the patient's body, thus giving rise to an erroneous measurement.

Although instruments which determine the hematocrit from the electrical resistance of the blood are convenient in that they afford a simple means of measurement, they are disadvantageous in that they are susceptible to error due to the changes in the resistivity of the plasma resulting from variations in plasma electrolyte concentration etc.

SUMMARY OF THE INVENTION

In light of the foregoing observations and description of the conventional hematocrit measuring instruments, the object of the present invention is to provide a hematocrit measuring instrument capable of continuous measurement and capable of highly accurate measurement even in the case where there are variations in the concentration of the plasma electrolyte.

The above object of the present invention is accomplished by providing a hemtocrit measuring instrument of the type which determines the hematocrit of blood from the electrical resistivity of the blood with a blood resistivity measurement device, an ultrafilter for filtering a part of the plasma from the blood, a filtrate resistivity measurement device for measuring the resistivity of the filtrate from the ultrafilter and an arithmetic circuit for calculating the hematocrit of the blood from the resistivities of the blood and the filtrate, whereby the hematocrit of the blood is continuously measured by connecting the hematocrit measuring instrument into a circulatory path for the blood outside the patient's body and calculating the hematocrit from the resistivities of the blood and the filtrate.

DESCRIPTION OF THE PREFERRED EMBODIMENTS

Figure 1:
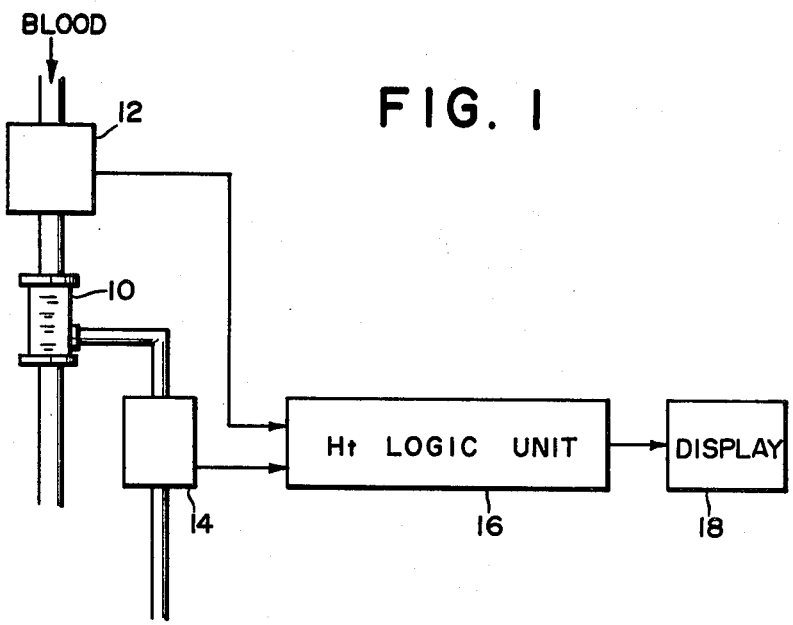
FIG. 1 is a block diagram of the hematocrit measuring instrument in accordance with the present invention.

The hematocrit measuring instrument in accordance with the present invention continuously measures the hematocrit of blood in a circulatory path outside the body, for example in a path for hemo-dialysis. The basic structure of the hematocrit measuring instrument is shown in FIG. 1. Through a path connected to the blood access of patient, blood is passed either under the patient's blood pressure or by a pump or the like. In the path are provided an ultrafilter 10 and a blood resistivity measurement device 12. The ultrafilter 10 has a semipermeable membrane through which a part of the blood plasma is ultrafiltered, with the filtrate being forwarded to a filtrate resistivity measurement device 14. The blood resistivity measurement device 12 and the filtrate resistivity measurement device 14 measure the electrical resistivities of the circulating blood and the blood filtrate, respectively, and forward the measured values to a hematocrit arithmetic circuit 16. The hematocrit arithmetic circuit 16 uses a formula expressing the relationship among the blood resistivity $\rho_b$, the filtrate resistivity $\rho_p$ and the hematocrit $H_t$ to calculate the hematocrit from the inputted $\rho_b$ and $\rho_p$. The calculated value is forwarded to a display 18.

Figure 2:
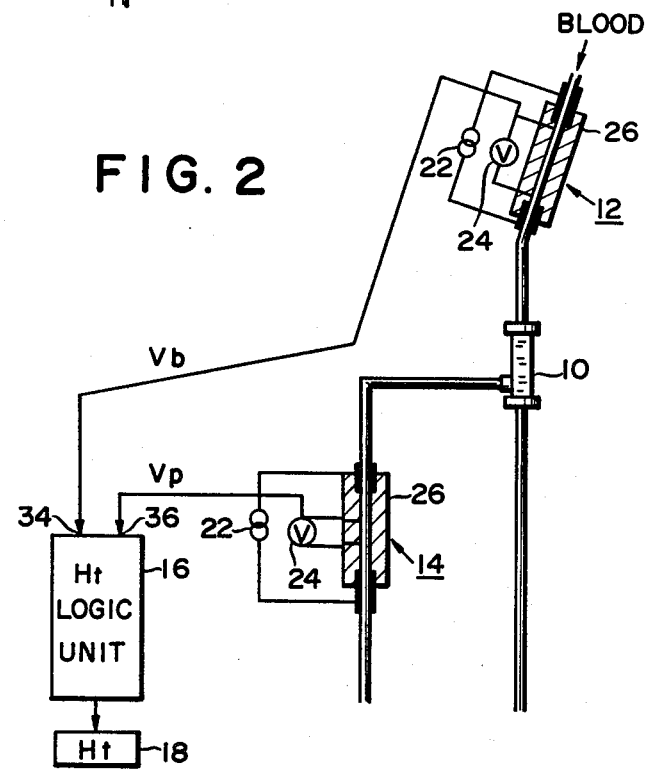
FIG. 2 is an explanatory view showing a first embodiment of the invention.

FIG. 2 shows a first embodiment of the invention more concretely and in greater detail. In this embodiment, the ultrafilter 10 is provided with a semipermeable membrane formed of polyacrylonitrile having a nominal cutoff at a molecular weight of 13,000. The semipermeable membrane operates to separate a part of the plasma from the blood.

Figure 3:
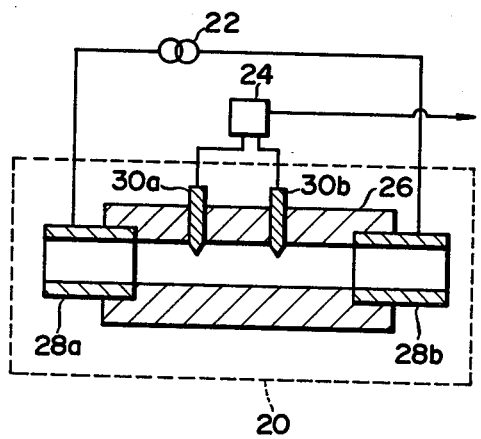
FIG. 3 is a diagram showing the structure of the electrical resistivity measurement device used for measuring the resistivity of blood and filtrate in the hematocrit measuring instrument in accordance with the present invention.

The blood resistivity measurement device 12 for measuring the resistivity of the blood, which is shown in detail in FIG. 3, is comprised of a resistance measurement cell 20, a constant AC current source 22 and an AC voltmeter 24. The resistance measurement cell 20 is provided with a polycarbonate pipe 26 which offers virtually no resistance to the blood flowing therethrough. At the opposite ends of this pipe 26 are provided cylindrical current electrodes 28a, 28b which also serve to connect the pipe 26 into the blood path. A pair of needle voltage electrodes 30a, 30b are provided in the pipe 26 between the cylindrical current electrodes 28a, 28b.

The constant AC current source 22 supplies a constant AC current between the current electrodes 28a, 28b. The AC voltmeter 24 converts the AC voltage arising between the voltage electrodes 30a, 30b, which is of the same frequency as the constant AC current source, into a DC voltage equal to 100/3 of the effective value of said AC voltage. As the current supplied between the current terminals by the constant AC current source 22 (hereinafter referred to as the measuring current) it is preferable to employ a weak, high frequency current from the point of the safety of the patient and the point of avoiding the effect of polarization. In the present embodiment there is used a current of 50 KHz and 30 μA rms. Moreover, since the hematocrit measuring instrument of the present invention measures the hematocrit of blood passing through a blood circulating path outside of the patient's body, for example a circulating path for hemo-dialysis, the overall blood circulating path into which the hematocrit measuring instrument is inserted in a closed loop including the patient. Therefore, the aforesaid measuring current flows not only through the resistance measurement cell 20 but also through the blood tubes, the patient etc. and the level of this current is inversely proportional to the total resistance of the current paths. In order to assure that the blood resistivity measurement device 12 will be able to measure the resistivity of the blood with high accuracy, the inner diameter of the pipe 26 is made as large as possible and the distance between the current electrodes 28a, 28b is made short so that the amount of measuring current flowing outside the resistance measurement cell 20 will be of such a small level compared to the amount of measuring current flowing inside the resistance measuring cell 20 as to be negligible.

In the blood resistivity measurement device 12, the resistivity $\rho_b$ of the blood flowing through the resistance measurement cell 20 is determined by the four-electrode method and a DC voltage $V_b$ having a magnitude proportional to the determined value is inputted to an input terminal 34 of the hematocrit arithmetic circuit 16.

It is a characteristic feature of the present invention that the filtrate resistivity measurement device 14 is provided separately of the blood resistivity measurement device 12. The filtrate resistivity measurement device 14, which is of exactly the same construction as the blood resistivity measurement device 12, produces a DC voltage $V_p$ proportional to the resistivity $\rho_p$ of the filtrate flowing through the resistance measurement cell 20 (the constant of proportionality being equal to that in the aforesaid blood resistivity measurement device) and inputs this DC voltage to an input terminal 36 of the hematocrit arithmetic circuit 16.

Figure 4:
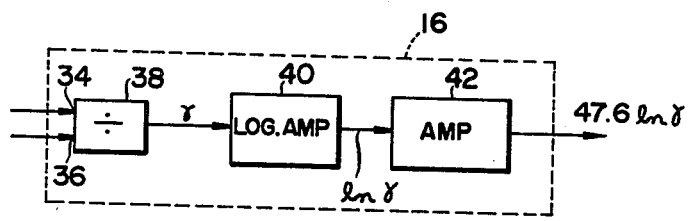
FIG. 4 is a diagram of the hematocrit arithmetic circuit used in the first embodiment of the invention.

The structure of the hematocrit arithmetic circuit 16 for calculating the hematocrit from the electrical resistivities of the blood and the filtrate is shown in FIG. 4. This circuit 16 consists of a divider 38, a logarithmic amplifier 40 and an ordinary linear amplifier 42. As the divider 38 there is used an ordinary analog divider which divides the voltage $V_b$ inputted to terminal 34 by the voltage $V_p$ inputted to terminal 36 and outputs the quotient $\gamma = V_b/V_p (=\rho_b/\rho_p)$ as a voltage signal. The logarithmic amplifier 40 converts the signal $\gamma = \rho_b/\rho_p$ received from the divider 38 into the logarithm ln $\gamma$. The linear amplifier 42 amplifies the value ln $\gamma$ $K_1$ times and outputs the hematocrit $H_t = K_1$ ln $\gamma$ to the display 18. It is advantageous to make $K_1$ equal 47.6.

The display 18 for displaying the measured hematocrit includes an A-D converter and a display panel. The analog signal received by the display 18 from the hematocrit arithmetic circuit 16 is A-D converted and the hematocrit $H_t$, i.e. the value $H_t = 47.6$ ln $(\rho_b/\rho_p)$, digitally represented as a percentage by the display 18.

Figure 5:
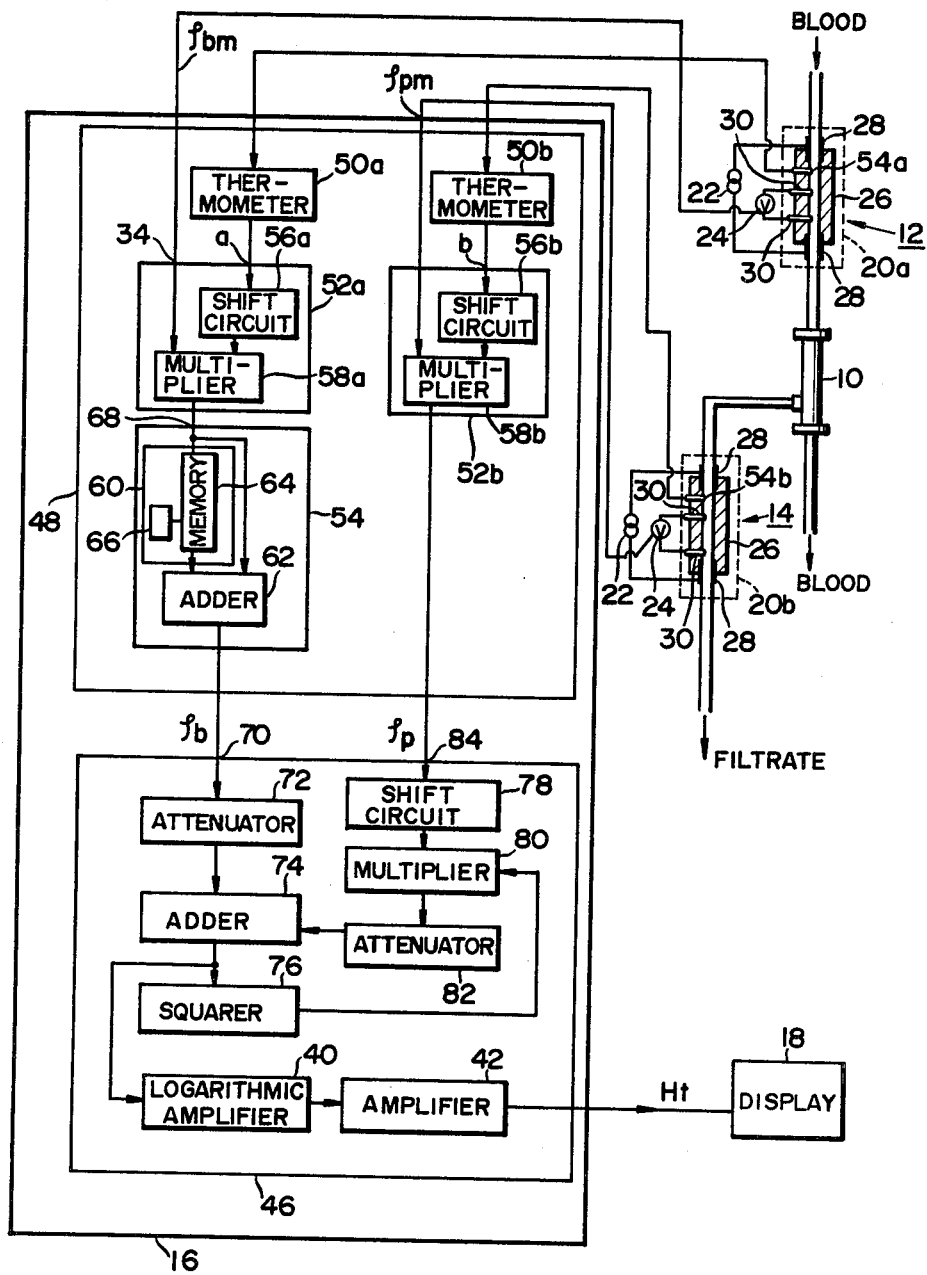
FIG. 5 is diagram showing a second embodiment of the invention.

It is known that the resistivities of blood plasma and blood vary with temperature at a rate of about $-2\%/°C.$, meaning that these resistivities become smaller with rising temperature. It has also been pointed out that the amount of change in the resistivity of blood caused by large changes in the sodium concentration of the blood plasma varies with the hematocrit value. Moreover, it is known that the orientation of blood cells that occurs when blood is in a flowing state causes the resistivity in the direction of blood flow to be less than that of blood which is at rest. In the first embodiment of the invention described above, if the blood and the filtrate are of the same temperature in the respective resistance measurement cells 20, if the blood is at rest, and if there is no extreme variation in the electrolytic concentration of the blood, it is possible to obtain an accurate measurement of the hematocrit. On the other hand, however, if a temperature difference should arise between the blood and the filtrate, if the blood should be in a flowing state or if there should be a major change in the sodium concentration of the blood or in any other factor causing a major change in its electrolytic concentration, an error will result in the measured hematocrit value. It is thus necessary to make it possible to obtain an accurate measurement of the hematocrit value even under such adverse conditions and this purpose is achieved by the second embodiment of the invention shown in FIG. 5.

In the following description of the second embodiment, components which are identical to those in the first embodiment are denoted by like reference numerals and further explanation thereof is omitted.

It is a characterizing feature of this second embodiment of the invention that thermistors 54a and 54b are provided respectively in the resistance measurement cells 20a, 20b of the blood resistivity measurement device 12 and the filtrate resistivity measurement device 14 and that the hematocrit arithmetic circuit 16 is provided with a compensation section.

The thermistor 54a is covered with an insulative cladding and is fitted onto the pipe 26 of the device 12 so as to face the blood path therein. The thermistor 54b is similarly provided in the device 14 so as to face the filtrate path. The outputs of the thermistors 54a and 54b are forwarded to thermometers 50a and 50b provided in the hematocrit arithmetic circuit 16.

The hematocrit arithmetic circuit 16 of this second embodiment consists of an arithmetic section 46 and a compensation section 48, the latter of which constitutes a characterizing feature of the invention. The compensation section 48 compensates the value of the blood resistivity $\rho_{bm}$ measured by the blood resistivity measurement device 12 for the effects of blood temperature and flow rate so as output to the arithmetic section 46 a resistivity value $\rho_b$ equivalent to that for blood at a temperature of 37° C. and in a state of rest. It also compensates the value of the filtrate resistivity $\rho_{pm}$ measured by the filtrate resistivity measurement device 14 for the temperature of the filtrate so as to output to the arithmetic section 46 a resistivity value $\rho_p$ for filtrate at a temperature of 37° C. To enable it to perform these compensations, the compensation section 48 is provided with the thermometers 50a, 50b, temperature compensators 52a, 52b and a flow rate compensator 54.

The thermometers 50a and 50b are respectively connected with thermistor 54a provided in the resistance measurement cell 20a of the blood resistivity measurement device 12 and the thermistor 54b provided in the resistance measurement cell 20b of the filtrate resistivity measurement device 14. They thus measure the blood temperature $T_b$ and the filtrate temperature $T_p$ and output signals $V_{Tb}$ and $V_{Tp}$ of magnitudes proportional to the measured values to the temperature compensators 52a and 52b.

The temperature compensator 52a is comprised of a shift circuit 56a and a multiplier 58a. The shift circuit 56a shifts the voltage $V_{Tb}$ received at the input terminal a by a reference voltage $V_o$, thereby producing a compensating voltage voltage $V_c$ which is output to the multiplier 58a. The multiplier 58a multiplies the two voltages input thereto and outputs the product to a flow rate compensator 54.

The resistivities of the plasma and the blood decrease about 2% for each 1° C. rise in temperature. Therefore, the resistivity of the blood at 37° C. can be conveniently calculated by the use of an arrangement wherein the thermometer 50a outputs a voltage of $-0.02 \times T$ volts for a measured temperature of T°C., the shift circuit 56a raises this voltage by $V_o = 1.74 \cdot (1+0.02 \times 37)$ volts to output a compensating voltage $V_c$ ($=1+0.02\times(37-T)$), and the multiplier 58a multiplies the voltage $V_b$ input to its input terminal 34 from the blood resistivity measurement device 12 by the compensating voltage $V_c$.

The temperature compensator 52b has exactly the same construction as the temperature compensator 52a and operates to convert the resistivity $\rho_{pm}$ of the filtrate at any given temperature to the filtrate resistivity $\rho_p$ at 37° C. As in the case of the temperature compensator 52a, the resistivity, temperature and compensating voltage are all processed as voltage signals.

The flow rate compensator 54 consists of a setting circuit 60 and an adder 62. The setting circuit 60 is made up of a memory 64 and a push-button switch 66. When the push-button switch 66 is pushed once, the voltage input to the input terminal 68 is stored in the memory 64 and when the push-button switch 66 is pushed a second time, the voltage input to the input terminal 68 at that time is subtracted from the stored voltage and the difference is stored in the memory 64 while being outputted to the adder 62. The value stored in the memory 64 can be reset by again pushing the push-button 66 to repeat the above operation.

The adder 62 adds the two voltages input thereto and outputs the sum to the input terminal 70 of the arithmetic section 46.

In view of the construction of the flow rate compensator described above, if the circulatory blood path is pinched with a clamp or the like at the beginning of the measurement operation to temporarily stop the blood flow and the push-button switch is pushed, and then, after the clamp has been removed to put the hematocrit measuring instrument in condition for continuous measurement of the hematocrit, the push-button switch is pushed again, the memory 64 will have been made to store the difference (referred to as $\Delta\rho$ hereinafter) in the resistivity of the blood between its flowing and still states. As a result the adder 62 will add the value $\Delta\rho$ to the resistivity of the flowing blood to obtain and output the resistivity of the blood at rest to the arithmetic section 46.

The arithmetic section 46 is a device for calculating the hematocrit $H_t$ from the resistivity $\rho_b$ of the blood at 37° C. and in the state of rest and the resistivity $\rho_p$ of the filtrate at 37° C. and is comprised of an attenuator 72, an adder 74, a squarer 76, a shift circuit 78, a multiplier 80, an attenuator 82, a logarithmic amplifier 40 and an amplifier 42. The attenuator 82 attenuates the voltage received at the input terminal 70 by a factor of $1/K_3$ ($K_3$ being a constant) and outputs the attenuated voltage to the adder which adds the voltages input from the attenuator 72 and the attenuator 82 and outputs the sum to the squarer 76 and the logarithmic amplifier 40. The squarer 76 squares the voltage input from the adder 74 and outputs the result to the multiplier 80. The shift circuit 78 subtracts the voltage input to the input terminal 84 from a constant voltage and outputs the difference to the multiplier 80. The multiplier 80 multiplies the voltage $K_3$ input from the shift circuit 78 and the voltage input from the squarer 76 and outputs the product to the attenuator 82. The attenuator 82 attenuates the voltage input from the multiplier 80 by a factor of $1/K_3$ and outputs the result to the adder 74. The logarithmic amplifier 40 converts the voltage input from the adder 74 to the logarithm thereof and outputs the result to the amplifier 42. The amplifier 42 amplifies the voltage input from the logarithmic amplifier 40 by a factor of $K_1$ ($K_1$ being a constant) and outputs the result to the display 18.

In the case of normal human blood in the state of rest, the relationship among the electrical resistivity of the blood $\rho_b$, the electrical resistivity of the blood plasma $\rho_p$ and the hematocrit $H_t$ can be expressed as:

$$\rho_b = \rho_p \, e^{\frac{1}{K_1} H_t} \tag{1}$$

or as:

$$H_t = K_1 \ln (\rho_b/\rho_p) \tag{2}$$

And it is known that normally at 37° C., $K_1 \approx 47$ and $\rho_p = K_3 \approx 54$ Ωcm.

In the case where sodium chloride is added to normal blood, the relationship between the change in the resistivity of the blood $\Delta\rho_b$ (Ωcm) and the hematocrit $H_t$ can be expressed as:

$$\Delta\rho_b \propto e^{\frac{1}{K_2} H_t}$$

From this it is seen that $K_2$ is approximately $\tfrac{1}{2}K_1$. Therefore, in a case where the sodium chloride concentration of the plasma has come to deviate from the normal value for a healthy person because of hemodialysis or the like, the relationship among the resistivity $\rho_b$ of the blood at 37° C. and in the state of rest, the resistivity $\rho_p$ of the blood plasma at 37° C. and the hematocrit $H_t$ can be approximated as:

$$\rho_b + (54 - \rho_p)\, e^{\frac{2}{K_1} H_t} = 54 e^{\frac{1}{K_1} H_t}$$

or as:

$$e^{\frac{1}{K_1} H_t} = \frac{\rho_b}{54} + \frac{(54 - \rho_p)\left(e^{\frac{1}{K_1} H_t}\right)^2}{54} \tag{3}$$

wherein $K_1 \approx 47$. The arithmetic section 46 uses this relationship to calculate $H_t$ from $\rho_b$ and $\rho_p$, and outputs the calculated value of $H_t$ to the display 18. More specifically, the shift circuit 78 first derives $(54-\rho_p)$ from $\rho_p$ of formula (3), whereafter the analog computation circuit consisting of the attenuator 72, the adder 74, the squarer 76 the multiplier 80 and the attenuator 82 derives $(1/_eK_1)H_t$ from $\rho_b$ of formula 3 and $(54-\rho_p)$. Next, the logarithmic amplifier 40 derives $(1/K_1)$Ht from the aforesaid $(1/_eK_1)H_t$ and the amplifier 42 calculates $H_t$ from the aforesaid $(1/K_1)H_t$. The display 18 is exactly the same as that in the first embodiment and is not described further here.

Although two specific embodiments of the present invention have been described above, the invention is not limited to these embodiments and may be modified in various ways within the scope of its technical concept.

For example, in the second embodiment, instead of using thermistors to detect the temperature of the blood and the filtrate it is possible to use transistor thermocouples or any other type elements capable of detecting temperature.

Also in the second embodiment, in a case where the flow rate of the blood changes continually so as to necessitate frequent adjustment of the compensation value, it is possible to replace the flow rate compensation section consisting of a setting circuit and an adder with one employing an electromagnetic or other type flowmeter capable of automatically supplying a compensation value for compensating the blood resistivity for flow rate.

It is further possible in the second embodiment to replace the analog calculation system used in the compensation section and the arithmetic section of the hematocrit arithmetic circuit with a digital system, and, even in the case of retaining the analog system, to employ different circuitry from that used in this second embodiment.

As explained in the foregoing, since in the present invention the hematocrit is calculated from the electrical resistivity of the blood and the electrical resistivity of the filtrate from the ultrafilter 10, measurement of the hematocrit can be carried out continuously and with high accuracy even in cases where there is some fluctuation in the concentration of the plasma electrolyte. Moreover, even in cases where there are large fluctuations in the concentration of the plasma electrolyte, where there is a temperature difference between the blood and the filtrate, where the blood is in a flowing state or where there is other cause for measurement error, it is still possible to carry out accurate measurement of hematocrit in accordance with the present invention by providing the arithmetic circuit 16 and the compensation section 48 and thus eliminating the erroneous factors.

What is claimed is:

1. A hematocrit measuring instrument wherein hematocrit is derived from the electrical resistivity of the blood comprising a blood resistivity measurement device, an ultrafilter for filtering a part of the plasma of the blood, a filtrate resistivity measurement device for measuring the resistivity of the filtrate from the ultrafilter and an arithmetic circuit for calculating the hematocrit of the blood from the resistivities of the blood and the filtrate, the hematocrit measuring instrument being connected into a circulatory path for the blood outside the patient's body for continuous measurement of hematocrit from the resistivities of the blood and the filtrate from the ultrafilter.

2. A hematocrit measuring instrument as claimed in claim 1 wherein the arithmetic circuit includes arithmetic circuitry capable of deriving the hematocrit $H_t$ from the electrical resistivity of the blood $\rho_b$ and the electrical resistivity of the filtrate $\rho_p$ in accordance with the formula:

$$H_t = K_1 \ln(\rho_b/\rho_p)$$

where $K_1$ is a constant.

3. A hematocrit measuring instrument as claimed in claim 1 wherein the arithmetic circuit includes arithmetic circuitry capable of deriving the hematocrit $H_t$ from the electrical resistivity of the blood $\rho_b$ and the electrical resistivity of the filtrate $\rho_p$ in accordance with the formula:

$$e^{-\frac{1}{K_1} H_t} = \frac{\rho_b}{54} + \frac{(54-\rho_p)\left(e^{-\frac{1}{K_1} H_t}\right)^2}{54}$$

where $K_1$ is a constant.

4. A hematocrit measuring instrument according to claim 1, further comprising a means for sensing the temperature of the blood, a means for sensing the temperature of the filtrate and a means for adjusting the measured resistivities of the blood and the filtrate in response to the temperatures of the blood and the filtrate.

* * * * *